United States Patent [19]

Eggers et al.

[11] Patent Number: 5,633,578
[45] Date of Patent: May 27, 1997

[54] ELECTROSURGICAL GENERATOR ADAPTORS

[75] Inventors: Philip E. Eggers, Dublin; Dennis J. Denen, Columbus, both of Ohio

[73] Assignee: Hemostatic Surgery Corporation, Georgetown, Cayman Islands

[21] Appl. No.: 275,598

[22] Filed: Jul. 15, 1994

Related U.S. Application Data

[63] Continuation-in-part of Ser. No. 210,090, Mar. 17, 1994, Pat. No. 5,472,443, which is a continuation of Ser. No. 877,533, Jun. 7, 1991, abandoned.

[51] Int. Cl.⁶ ............................................. A61B 17/39
[52] U.S. Cl. ........................... 323/301; 606/38; 323/911
[58] Field of Search ..................... 606/50, 40, 41, 606/46, 49, 142, 143, 211, 32, 34, 37; 323/91

[56] References Cited

U.S. PATENT DOCUMENTS

| | | | |
|---|---|---|---|
| 1,586,645 | 6/1926 | Bierman | 128/303.14 |
| 3,651,811 | 3/1972 | Hildebrandt et al. | 128/303.17 |
| 3,685,518 | 8/1972 | Beuerle et al. | 128/303.17 |
| 3,730,188 | 5/1973 | Ellman | 128/303.14 |
| 3,875,945 | 4/1975 | Friedman | 128/303.14 |
| 3,980,085 | 9/1976 | Ikuno | 128/303.17 |
| 4,005,714 | 2/1977 | Hiltebrandt | 128/303.17 |
| 4,030,501 | 6/1977 | Archibald | 128/303.14 |
| 4,041,952 | 8/1977 | Morrison, Jr. et al. | 128/303.13 |
| 4,054,143 | 10/1977 | Bauer | 128/303.17 |
| 4,092,986 | 6/1978 | Schneiderman | 128/303.14 |
| 4,154,240 | 5/1979 | Ikuno et al. | 128/303.14 |
| 4,196,734 | 4/1980 | Harris | 128/303.14 |
| 4,232,676 | 11/1980 | Herczog | 128/303.14 |
| 4,338,940 | 7/1982 | Ikuno | 128/303.14 |
| 4,370,980 | 2/1983 | Lottick | 128/303.17 |
| 4,492,231 | 1/1985 | Auth | 606/40 |
| 4,590,934 | 5/1986 | Malis et al. | 128/303.14 |
| 4,651,734 | 3/1987 | Doss et al. | 128/303.14 |
| 4,657,016 | 4/1987 | Garito et al. | 128/303.13 |
| 4,658,819 | 4/1987 | Harris et al. | 128/303.14 |
| 4,685,459 | 8/1987 | Koch et al. | 128/303.17 |
| 4,752,864 | 6/1988 | Clappier | 363/86 |
| 4,862,890 | 9/1989 | Stasz et al. | 128/303.14 |
| 4,903,696 | 2/1990 | Stasz et al. | 606/37 |
| 4,938,761 | 7/1990 | Ensslin | 606/31 |
| 4,958,539 | 9/1990 | Stasz et al. | 76/104.1 |
| 4,961,739 | 10/1990 | Thompson | 606/37 |
| 4,969,885 | 11/1990 | Farin | 606/38 |

FOREIGN PATENT DOCUMENTS

| | | | |
|---|---|---|---|
| 0 210 125 | 7/1986 | European Pat. Off. | A61B 17/39 |
| 0 316 469 | 11/1987 | European Pat. Off. | A61B 17/39 |
| 0 341 446 | 4/1989 | European Pat. Off. | A61B 17/39 |
| 2 536 924 | 6/1984 | France | H03K 21/36 |
| 2 647 683 | 7/1990 | France | A61N 1/06 |
| 854366 | 8/1981 | U.S.S.R. | |
| 2 038 167 | 7/1981 | United Kingdom | A61B 17/36 |
| 2 066 104 | 7/1981 | United Kingdom | B32B 5/14 |
| 2 161 082 | 8/1986 | United Kingdom | A61B 17/36 |
| 2 213 381 | 8/1989 | United Kingdom | A61B 17/39 |

OTHER PUBLICATIONS

"Electrosurgical Units", Evaluation, Health Devices, Sep.–Oct. 1987, pp. 291–342.

Bovie 400 SR Electrosurgical Unit, 3 page product description, Clinical Technology, Division of Sybron Corporation, date circa 1987.

(List continued on next page.)

*Primary Examiner*—Aditya Krishnan
*Attorney, Agent, or Firm*—Fish & Neave; Nicola A. Pisano

[57] ABSTRACT

Adaptors are provided for use with electrosurgical bipolar instruments and standard commercially available electrosurgical generators that reduce coagulum buildup and sticking on electrosurgical instruments. A first type of adaptor converts a high voltage, high crest factor output voltage waveform typical of conventional electrosurgical generators to a more desirable lower voltage, lower crest factor regime. A second type of adaptor limits the peak open-circuit voltage supplied by a conventional electrosurgical generator to an electrosurgical instrument.

10 Claims, 6 Drawing Sheets

OTHER PUBLICATIONS

Model 9600 and Model 9601 Electrosurgery Generator, Specifications and Features, 1 page product specification, Concept Electrosurgical Products, date circa 1987.

Model 744 Electrosurgical Generator, 1 page product specification, The Birtcher Corporation, date circa 1987.

*Neomed Omega Electrosurgical Generator,* 2 page product description, Neomed, Inc., date circa 1987.

Valeylab SSE2L Isolated Electrosurgical Generator, 2 page product description, Valleylab, Inc., date circa 1987.

*Valleylab Force 2 Electrosurgical Generator,* 1 page product description, Valeylab, Inc., date circa 1987.

*The Bovie X-10 Electrosurgical Unit,* 1 page product description, Clinical Technology, date circa 1987.

*Power Units, Accessories, Aspen FM380, MF360B, MF180A Electrosurgical Units,* 2 page product description, Aspen Labs, Inc., date circa 1987.

*Micro 180 Specifications,* 2 page product description, Aspen Labs, Inc., date circa 1987.

Specification Summary, Aspen MF360A, 1 page product description, Aspen Labs, Inc., date circa 1987.

ELECTROSURGICAL GENERATOR ADAPTORS

This application is a continuation-in-part of and commonly assigned U.S. patent application Ser. No. 08/210,090, entitled "Electrosurgical Apparatus For Employing Constant Voltage And Methods Of Use," filed Mar. 17, 1994 U.S. Pat. No. 5,472,443, which is a continuation of U.S. patent application Ser. No. 07/877,533, filed Jun. 7, 1991, abandoned.

This invention relates to adaptors for use with conventional electrosurgical generators to provide voltage output waveforms effective in reducing coagulum buildup, and to alleviate sticking, on hemostatic electrosurgical instruments.

BACKGROUND OF THE INVENTION

Hemostatic bipolar electrosurgical techniques are known for reducing bleeding from incised tissue prior to, during, and subsequent to incision. Such techniques generally pass a high voltage-high frequency current through a patient's tissue between two electrodes for cutting and coagulating the tissue. This current causes joulean heating of the tissue as a function of the current density and the resistance of the tissue. Heat deposited in the tissue coagulates the blood in the vessels contained in the tissue, thus reducing the blood flow from severed vessels and capillaries.

In previously known electrosurgical systems, a generator typically supplies a high voltage, high frequency voltage waveform to an electrosurgical instrument to cause a current to pass through the patient's tissue in the form of a high voltage electric arc. A drawback of such systems, however, is the tendency of the current arc to promote charring of the tissue, thus inhibiting rapid regrowth of the tissue.

Another drawback of previously known electrosurgical systems is a tendency of the coagulated blood and severed tissue to adhere to the working surfaces of the instrument, due to wide variations in peak-to-peak voltage waveform supplied by the generators. This "coagulum" buildup increases the electrical resistance of the path along which current flowing between the electrodes of the electrosurgical instrument must travel, resulting in reduced hemostasis, ineffective cutting action, or both.

Yet another drawback of previously known electrosurgical systems is a tendency of tissue to adhere to the instrument as a result of initially high open-circuit voltages that occur when an electrosurgical instrument, powered by a conventional generator, is energized before the instrument electrodes are brought into contact with the patient's tissue. This "sticking" problem can limit maneuverability of the instrument and cause tearing of previously congealed tissue, thereby reactivating blood flow from that tissue.

Previously known electrosurgical generators typically provide monopolar and bipolar modes of operation in which they supply high frequency (above 100 kHz) alternating-current (AC) voltages in the range of 150 to 5000 volts peak-to-peak (or higher) at power ratings of less than 400 watts. The highest levels of peak-to-peak voltages typically result from energizing the electrosurgical generator before the electrodes are brought into contact with tissue. Examples of such generators are provided in Malis et al. U.S. Pat. No. 4,590,934, Schneiderman U.S. Pat. No. 4,092,986, Farin U.S. Pat. No. 4,969,885. See also, for example, the Operator's Manual for the Valleylab Force 2® and Force 4® generators.

There are in addition some previously known special purpose electrosurgical generators for reducing coagulum buildup and sticking when used with particular instruments. For example, Herczog U.S. Pat. No. 4,232,676 describes an electrosurgical scalpel and a special purpose low voltage generator in which power supplied to the scalpel is regulated by varying the frequency of the output voltage waveform. Similarly, Auth U.S. Pat. No. 4,492,231 describes a bipolar coagulator and special purpose low impedance generator that provides a low crest factor, low output voltage waveform to the coagulator to reduce coagulum buildup and sticking.

A drawback inherent in the electrosurgical systems described in the aforementioned Herczog and Auth patents is that each requires a special purpose electrosurgical generator which is developed for the particular electrosurgical instruments described in those patents. Likewise, any advantages provided by the generators described in the above-mentioned patents are offset by the practical consideration of having to purchase such generators, rather than being able to modify a large installed base of more conventional generators.

It would therefore be desirable to provide simple to use, low-cost adaptors for use with standard commercially available electrosurgical generators that would reduce problems with coagulum buildup and sticking encountered when using most electrosurgical instruments.

It further would be desirable to provide adaptors that could be connected between the monopolar or bipolar output jacks of standard commercially available electrosurgical generators and most electrosurgical instruments to modify the voltage waveforms supplied to the instruments to reduce coagulum buildup and sticking problems.

SUMMARY OF THE INVENTION

In view of the foregoing, it is an object of this invention to provide simple to use, low-cost adaptors for use with standard commercially available electrosurgical generators that reduce problems with coagulum buildup and sticking encountered when using most electrosurgical instruments.

It is a further object of the present invention to provide adaptors that can be connected between the monopolar or bipolar output jacks of standard commercially available electrosurgical generators and most electrosurgical instruments to modify the voltage waveforms supplied to the instruments to reduce coagulum buildup and sticking problems.

These and other objects are accomplished in accordance with the principles of the present invention by providing adaptors for use with standard commercially available power supplies to perform a number of waveform conditioning operations, depending upon the generator output and the desired waveform characteristics for a particular electrosurgical instrument.

In a first embodiment of the present invention, an adaptor is provided which may be connected to the monopolar or bipolar output jacks of a variety of conventional electrosurgical generators. The adaptor continuously modifies the voltage waveform provided by those generators to supply a substantially constant low voltage, low crest factor output to an electrosurgical instrument as described in above-mentioned copending and commonly assigned U.S. application Ser. No. 08/210,090, entitled "Electrosurgical Apparatus For Employing Constant Voltage And Methods Of Use," filed Mar. 17, 1994, which is incorporated herein by reference.

In an alternative embodiment of the present invention, an adaptor is provided which may be preferably connected to the bipolar output jacks of a variety of previously known electrosurgical generators to limit the peak open-circuit voltages supplied to the electrosurgical instrument. Applicants have determined that coagulum buildup and sticking problems can be greatly alleviated by providing an adaptor that limits primarily the peak open-circuit voltage experienced by an electrosurgical instrument, rather than modifying the output voltage continuously. Thus, as compared to the first described embodiment of the present invention, which modifies the output voltage even when the instrument is under load, this alternative embodiment serves to limit mainly the open-circuit voltage (i.e., that experienced when the instrument is energized before being brought into contact with the tissue).

BRIEF DESCRIPTION OF THE DRAWINGS

The above and other objects and advantages of the invention will be apparent upon consideration of the following detailed description, taken in conjunction with the accompanying drawings, in which like reference numerals refer to like parts throughout, and in which.

DETAILED DESCRIPTION OF THE INVENTION

Applicants have determined that coagulum buildup and sticking encountered with hemostatic bipolar instruments may be reduced in two ways. A first method is described in copending and commonly assigned U.S. patent application Ser. No. 08/210,090, filed Mar. 17, 1994, as a continuation of U.S. patent application Ser. No. 07/877,533, abandoned, the text of which is incorporated herein by reference. In that application, applicants teach that coagulum buildup and sticking problems encountered with previously known electrosurgical systems can be reduced by employing electrosurgical generators having "stiff" output characteristics, and by using voltage waveforms having substantially constant low voltage (10–130 VRMS) and crest factors near unity.

In addition, applicants have discovered that coagulum buildup and sticking problems encountered with bipolar electrosurgical instruments can be reduced simply by limiting the peak open-circuit voltages supplied to electrosurgical instruments. In this second method, applicants have determined that much coagulum buildup, sticking and arcing can be eliminated by ensuring that the peak open-circuit voltage (that developed when the instrument is energized before contacting the tissue) supplied to the instrument electrodes or tissue does not exceed about 200 Vpeak (400 Vpeak-to-peak).

Applicants appreciated that in order to provide the reduced coagulum and sticking benefits of their low voltage/low crest factor/low impedance and voltage limiting techniques to the widest variety of electrosurgical instruments at low cost, it was most advantageous to modify the voltage waveform outputs of standard commercially available electrosurgical generators using adaptors to implement applicants' techniques.

Figure 1:
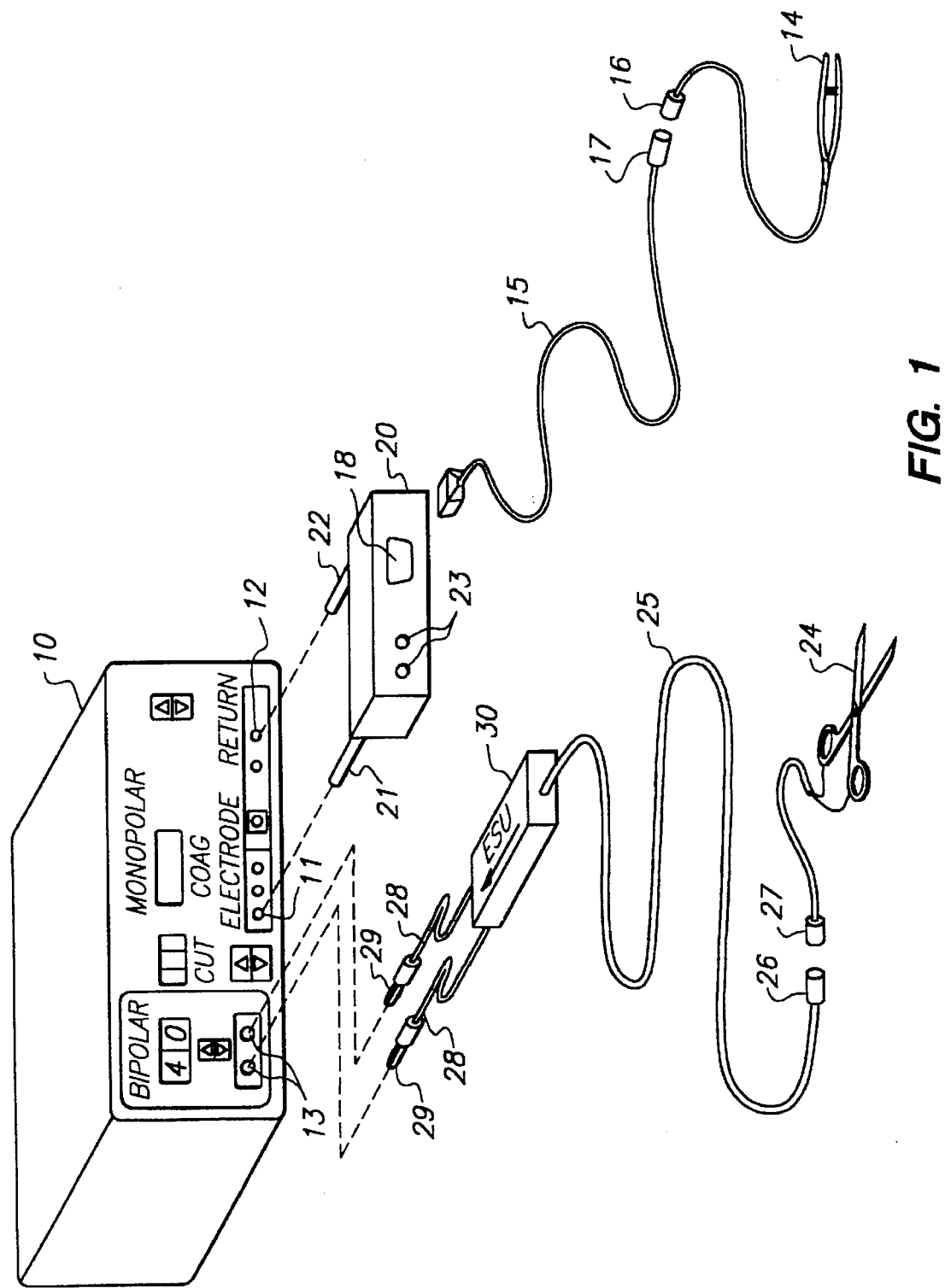
FIG. 1 is a perspective view of a standard commercially available electrosurgical generator showing illustrative adaptors constructed in accordance with the present invention connected to it.

Referring to FIG. 1, a conventional electrosurgical generator 10 is shown having monopolar output jack 11, return jack 12 and bipolar output jacks 13. Electrosurgical generator 10 may be, for example, a Valleylab Force 4®, Force 2® or other similar electrosurgical generator such as those commercially available from Valleylab, Aspen, Clinical Technology or Neomed. For use with the present invention, generator 10 preferably should be generally capable of developing in the range of at least 50 watts power in the bipolar mode and have maximum open-circuit peak-to-peak voltages less than about 2000 V in bipolar mode and less than 5000 V in monopolar cut mode.

By way of illustration of use of the present invention when connected to the monopolar output stage of a conventional electrosurgical generator, bipolar coagulating forceps 14 is detachably connected to supply cable 15 via connectors 16 and 17. Supply cable 15 in turn plugs into receptor 18 of adaptor 20 constructed in accordance with a first embodiment of the present invention. Adaptor 20 includes plugs 21 and 22 which connect directly to monopolar output jack 11 and return electrode jack 12. Adaptor 20 accepts a high frequency high voltage (about 2000 Vpeak) output waveform from generator 10 (operating in "cut mode", i.e., with a sine wave output having a crest factor of less than about 2.0) via jacks 11 and 12 and supplies a waveform to bipolar forceps 14 having a voltage in the range of 10–130 VRMS with a crest factor less than or equal to about 1.4. Adaptor 20 may include LED status indicators 23.

Still referring to FIG. 1, bipolar scissors 24, constructed as described in commonly assigned U.S. Pat. No. 5,324,289, are detachably connected to supply cable 25 via connectors 26 and 27. Cable 25 extends from adaptor 30 constructed in accordance with a second embodiment of the present invention. Adaptor 30 preferably connects to bipolar output jacks 13 of generator 10 by leads 28 terminating in "banana" plugs 29 or other suitable connection means. Adaptor 30 accepts a high frequency high voltage output waveform (e.g., about 2000 Vpeak-to-peak) from generator 10 via bipolar output jacks 13 and supplies a waveform to bipolar scissors 14 having a voltage which does not exceed about 350–400 Vpeak-to-peak. Adaptor 30 according to this embodiment of the present invention suppresses any initially high open-circuit voltages, occurring for example, when the scissors are energized before they contact a patient's tissue.

Figure 2:
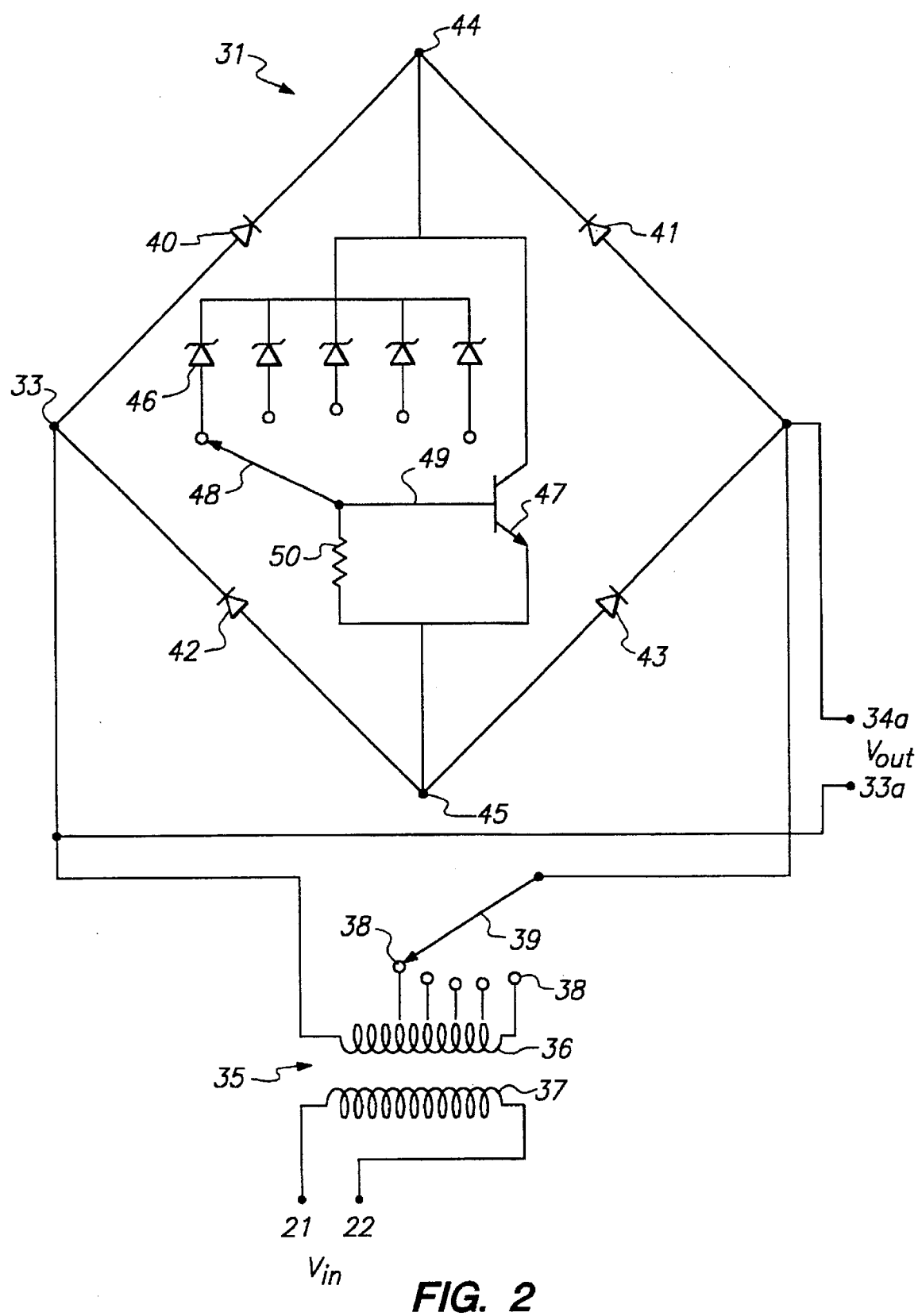
FIGS. 2 is a circuit diagram for a voltage conditioning adaptor that connects to the monopolar output jacks of standard commercially available electrosurgical generators as shown in FIG. 1 to provide a low voltage, low crest factor output voltage waveform.

Referring now to FIG. 2, circuit 31 of adaptor 20 is described. In accordance with the techniques described in copending and commonly assigned U.S. patent application Ser. No. 07/877,533, circuit 31 supplies a substantially constant voltage alternating-current (AC) waveform to the connected electrosurgical instrument, wherein the waveform has a crest factor near unity (substantially less than about 1.4) and the voltage is in the range of 10–130 volts RMS.

Adaptor 20 may have its terminals 21 and 22 configured to permit attachment of the adaptor to any of several widely commercialized electrosurgical generators, such as the above-described Valleylab units or the Neomed model 3000. Adaptor 20, through circuit 31, provides an output voltage waveform having the above-mentioned characteristics by "clipping" the peaks of sinusoidal waveforms while simultaneously reducing the voltage input from the conventional electrosurgical generator. Whereas the monopolar output waveforms of conventional electrosurgical generators commonly have pure sinusoidal shapes, circuit 31 supplies a substantially constant voltage level to the electrosurgical instrument during the "peaks" of the sine waveform, so that the resulting output waveform has a crest factor near unity and generally less than about 1.10.

Circuit 31 also reduces the output impedance from the perspective of the attached electrosurgical instrument. Since impedance is proportional to the square of the voltage, the generally five-fold reduction in output voltage under load also causes a 25-fold decrease in the impedance of the source. Accordingly, a conventional power supply having an output impedance of 300 ohms when connected to an electrosurgical instrument via circuit 31 of the present invention, will appear to have an output impedance of only 12 ohms. Thus, the output voltage waveform supplied by adaptor 20 of a previously known electrosurgical generator will not be subject to the impedance-induced voltage excursions that occur with conventional electrosurgical generators alone.

Circuit 31 receives a high voltage AC input power signal at input terminals 21 and 22 from the output of a previously known electrosurgical generator, such as one of those shown described above, and provides a low voltage, low crest-factor AC output voltage waveform at output terminals 33 and 34. The electrosurgical instrument is connected to output terminals 33a and 34a. The input signal is converted to the output signal by first adjusting the voltage downward to roughly the output level desired and second, clipping what is typically a sine wave signal near its peaks to produce a low crest-factor waveform. Because circuit 31 uses polarity-sensitive elements—a transistor and diodes—the applied power must first be rectified to avoid reverse biasing these elements.

The input signal is stepped down to a lower peak-to-peak voltage level at nodes 33 and 34 by transformer 35. The voltage between nodes 33 and 34 is determined by the ratio between the number of windings on secondary 36 and the number of windings on primary 37. Preferably, multiple taps 38 are provided, each having a different secondary to primary ratio, to accommodate various input voltage levels and therefore, various of the commercially available electrosurgical generators. The step-down ratio may therefore be adjusted by selecting the appropriate tap, for example, by switch 39. If the voltage input signal is not stepped-down significantly, larger amounts of power will be dissipated during clipping, leading to a relatively low conversion efficiency for the adaptor-generator combination, although this will produce a low crest-factor output. On the other hand, if a high step-down ratio is selected, little clipping will occur, resulting in a relatively high conversion efficiency, though the output signal will have a somewhat higher crest-factor.

In operation, the stepped-down AC waveform between nodes 33 and 34 is rectified by diodes 40, 41, 42 and 43. When the voltage at node 33 is higher than that at node 34, diodes 40 and 43 turn on, allowing the signal at node 33 to be passed to nodes 44 and 45. For voltages below the breakdown voltage of the selected Zener diode 46, little current is conducted and transistor 47 remains off, representing a high impedance between nodes 44 and 45. Thus, current flows primarily through output terminals 33a and 34a and the electrosurgical instrument and tissue disposed therebetween. No current flows through reverse biased diodes 41 and 42. When the polarity of the AC waveform shifts during the latter part of the waveform cycle, a low current passes through diodes 41, 42 and the peak clipping elements; no current then passes through reverse biased diodes 40 and 43.

The maximum output voltage provided between output terminals 33a and 34a is determined by selecting one of Zener diodes 46, each of which has a different breakdown voltage, with switch 48. When the voltage at node 44 rises to the Zener breakdown voltage (typically ranging from 30 to 100 volts) of the selected one of Zener diodes 46, current is conducted through this diode causing transistor 47 to turn on. When on, transistor 47 provides a lower impedance path from node 44 to node 45 than that across output terminals 33a and 34a. When transistor 47 is turned on, it acts to shunt current from the output terminals and prevents the voltage between terminals 33a and 34a from rising. If this voltage begins to rise, the selected one of Zener diodes 46 conducts additional current into base 49, further turning on transistor 47, thereby reducing its impedance and causing it to pass more current. The greater current flow limits the voltage rise between terminals 33a and 34a.

Figure 3:
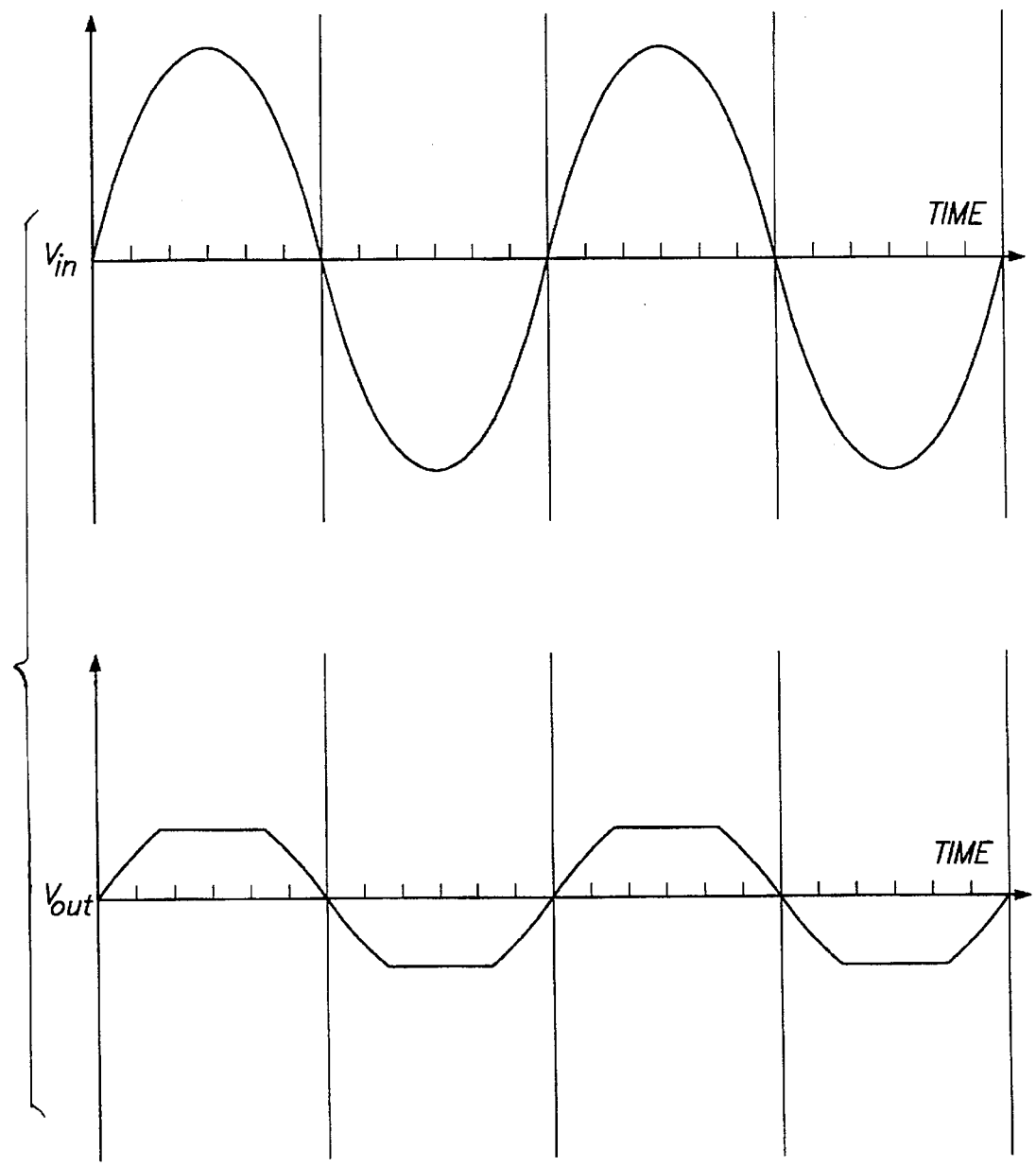
FIG. 3 shows a comparison of the input and output voltage waveforms obtained from the adaptor constructed in accordance with FIG. 2.

The voltage at output terminal 33a remains constant until later in the AC cycle, when the voltage at node 33, and therefore output terminal 44, falls. The selected one of Zener diodes 46 then ceases to conduct current into base 49, turning transistor 47 off. Due to the symmetry of circuit 31, when the voltage at node 34 rises to the Zener breakdown voltage, the voltage output at output terminal 34a is similarly clipped. The transformation of the input voltage waveform from the electrosurgical generator to the output voltage waveform of the adaptor 20 is shown in FIG. 3.

In a preferred embodiment of circuit 31, multiple taps 38 of transformer 35 have primary to secondary winding ratios in the range of 4:1 to 7:1, thus causing a factor of 4 to 7 reduction in voltage. Diodes 40–43 are rated at 6 A and may be commonly packaged as a bridge rectifier. Transistor 47 is an npn transistor having a 20 A capacity, such as PN 2SC3281 available from Motorola Corporation of Schaumburg, Ill. Resistor 50 has a resistance of 620Ω.

One skilled in the art of circuit design will appreciate that circuit 31 could be readily modified to use multiple transistors to increase shunt current capability or to modify the shunt circuit to employ pnp devices. In addition, one skilled in the art of circuit design will also appreciate that circuit 31 could be readily modified for use with the bipolar output jacks of a standard commercially available electrosurgical generator instead of the monopolar output jacks. In that case, a smaller transformer could be used (or even none at all), while the voltage limiting circuit could still be used to provide the desired voltage reduction described above.

Figure 4:
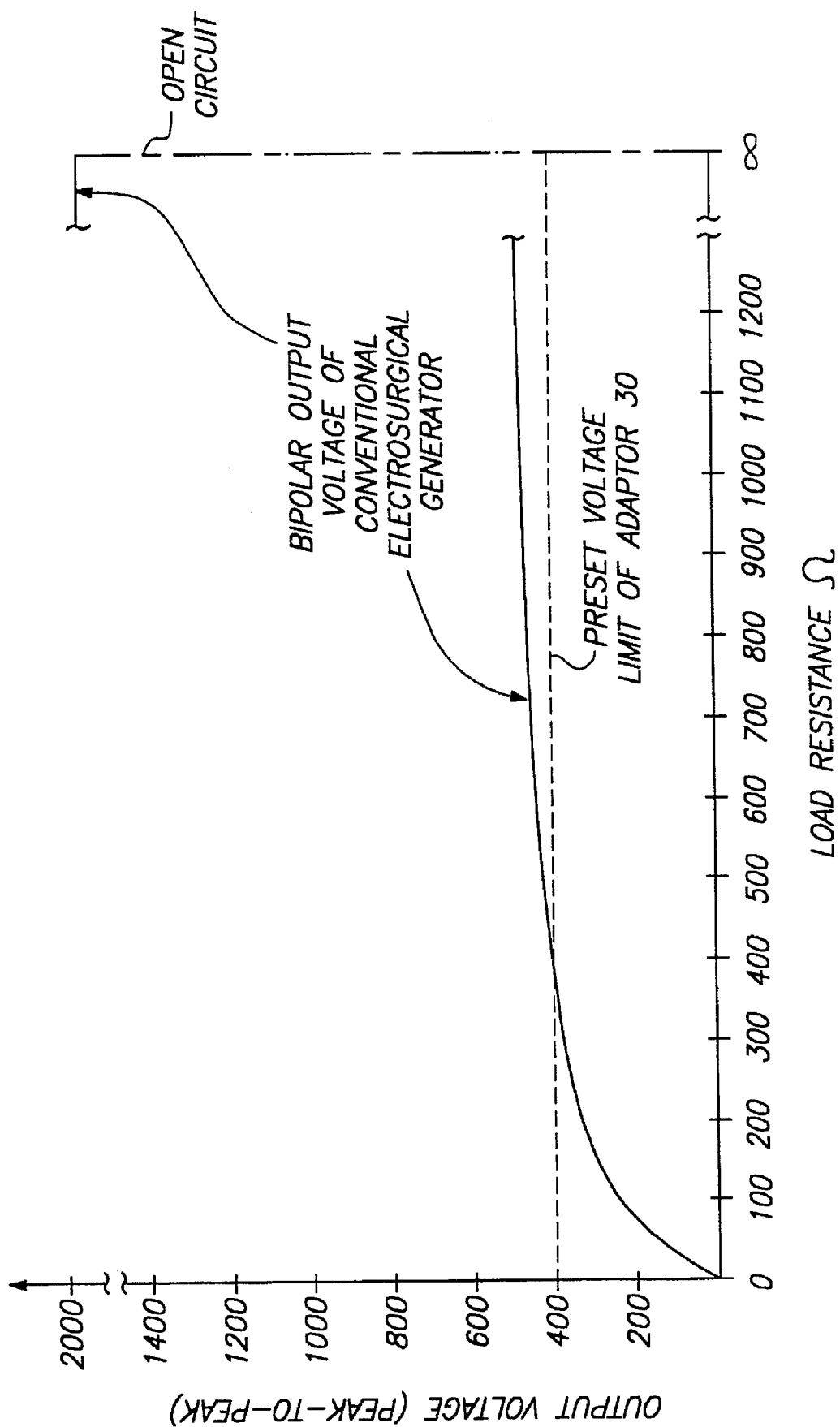
FIG. 4 is a diagram showing the output peak voltage versus load resistance for an open-circuit voltage limiting adaptor in accordance with the present invention.
Figure 5:
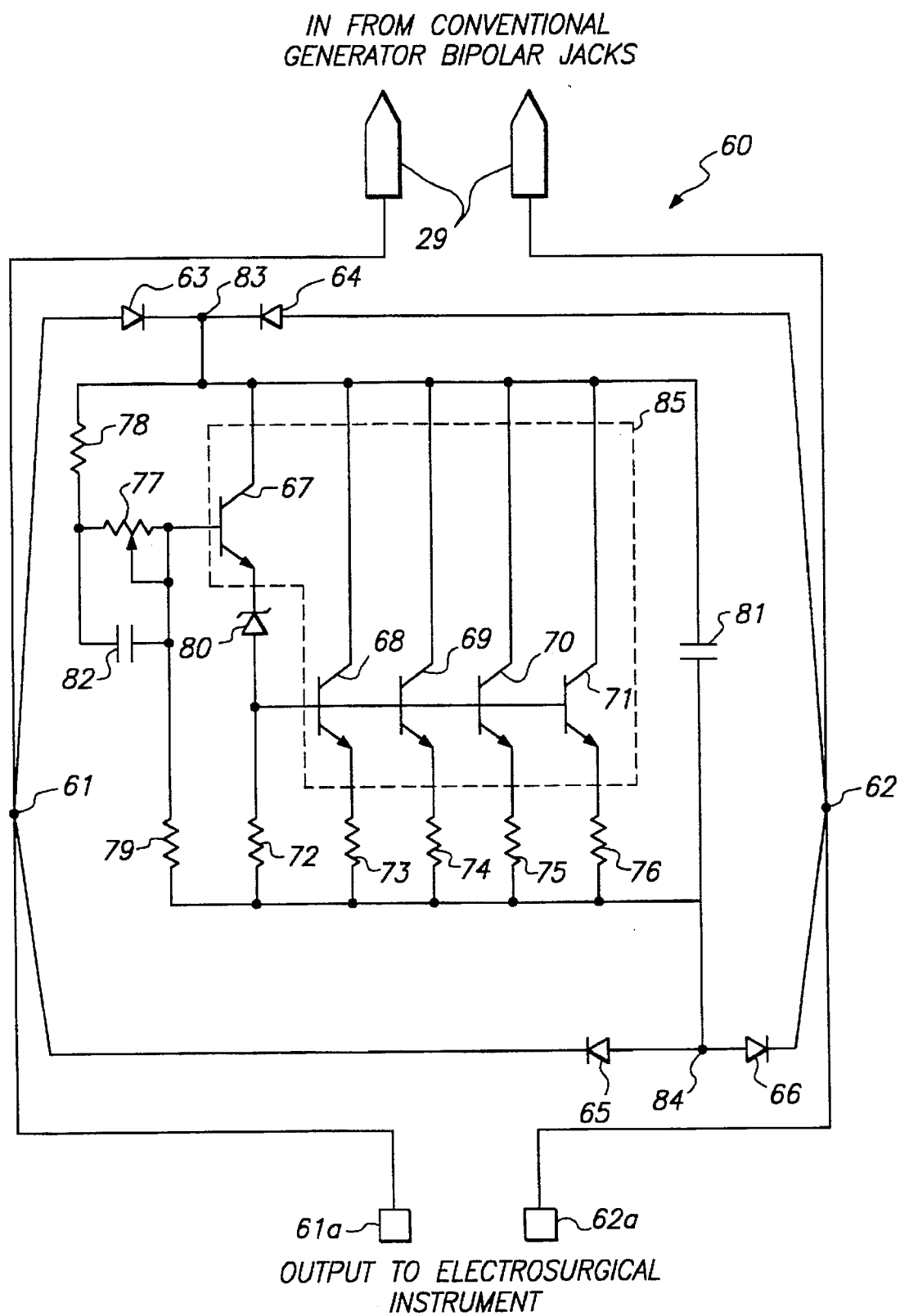
FIG. 5 is a circuit diagram for a open-circuit voltage limiting adaptor that connects to the bipolar output jacks of standard commercially available electrosurgical generators as shown in FIG. 1 to limit the open-circuit output voltage waveform.

Referring now to FIGS. 4 and 5, circuit 60 of adaptor 30 constructed in accordance with a second embodiment of the present invention is described. The adaptor constructed in accordance with this embodiment of the invention differs from adaptor 20 described hereinabove in that whereas adaptor 20 continuously modifies the voltage waveform output by the generator, adaptor 30 serves primarily to limit open-circuit voltages supplied to the electrosurgical instrument.

Circuit 60 preferably accepts a bipolar output waveform from a standard commercially available electrosurgical generator, such as the Valleylab units discussed above. Circuit 60 "clips" the waveform voltage peaks produced by the conventional generator to limit the open-circuit voltage supplied to the electrosurgical instrument to a value in a lower range, for example, from 350 to 400 Vpeak-to-peak.

Unlike circuit 31 of adaptor 20, circuit 60 omits a transformer, and thus does not provide the impedance-reducing capabilities of adaptor 20. Moreover, because adaptor 30 limits mainly open-circuit voltages, adaptor 30 does not significantly modify the output voltage waveform when the instrument is conducting current to the tissue (i.e., under load). Thus, power delivery to the tissue for load resistances of 100 to 200 ohms (typical of the range encountered in contacting tissue) is not significantly effected. As the load resistance increases above 300 to 400 ohms, circuit 60 prevents the output voltage from rising above the predetermined level of 350 to 400 Vpeak-to-peak, as shown in FIG. 4.

Applicants have determined that even without continuous waveform conditioning as provided by circuit 31, circuit 60 provides satisfactory operation when used, for example, with the Metzenbaum-style bipolar scissors described in commonly assigned U.S. Pat. No. 5,324,289.

Applicants have further determined that adaptor 60 (when set at 200 Vpeak), when used in conjunction with a Valleylab Force 4® generator set to 70 W in the "Precise" Mode, enables the above-described Metzenbaum-style bipolar scissors to be successfully used at output voltage levels provided by conventional electrosurgical generators. In particular, applicants have determined that using adaptor 30 in such a manner, excellent hemostasis and cutting action can be obtained with those scissors without experiencing insulation degradation, current arcing, coagulum buildup or sticking.

Referring now to FIG. 5, circuit 60 receives a high voltage AC input voltage waveform at input terminals 29 from the output of a previously known electrosurgical generator such as those described above, and provides an AC output waveform at output terminals 61 and 62 in the range of about 350 to 400 Vpeak-to-peak. The electrosurgical instrument is connected across output terminals 61a and 62a. The input voltage waveform is converted to the output voltage waveform by limiting the input voltage waveform when it exceeds a predetermined value (e.g., 400 Vpp). Because circuit 60 uses polarity sensitive elements—transistors and diodes—the applied signal is first rectified to avoid reverse biasing these elements.

Still referring to FIG. 5, circuit 60 comprises a full wave bridge rectifier of fast 200 V, 6 A diodes 63, 64, 65 and 66. Power transistor 67 is used to regulate the adaptor while bypass transistors 68, 69, 70, and 71 and resistors 72, 73, 74, and 75 act as current passing elements. Potentiometer 77, in conjunction with the value selected for resistors 78 and 79, may be used to "tune" the peak voltage level at which the input waveform is clipped. Potentiometer 77 and resistors 78 and 79 form a voltage divider which determines the bias voltage supplied to the base of transistor 67. Zener diode 80, in conjunction with the above bias circuit determines the voltage at which bypass transistors 68–71 turn on in response to the voltage across nodes 83 and 84. Elements 77–80 therefore act as a switching circuit since they determine when bypass transistors 68–71 are turned on and off. Capacitors 79 and 82 filter out high frequency voltage fluctuations caused by switching transients. All five transistors 67–71 are mounted on heat sink 85 to dissipate the power "clipped" from the top of the input voltage waveform.

In operation, the input AC waveform is rectified by diodes 63, 64, 65 and 66. When the voltage at 61 is higher than that at node 62, diodes 63 and 66 turn on, allowing the signal at node 61 to be passed to nodes 83 and 84. Below about 400 Vpp (depending upon the setting of potentiometer 77), the base-emitter junction is not forward biased, so transistor 67 remains off, representing a large impedance between nodes 83 and 84. Thus, current flows primarily through output terminals 61a and 62a and the electrosurgical instrument and tissue disposed therebetween. No current flows through reverse biased diodes 64 and 65. When the polarity of the AC waveform shifts during the latter part of the waveform cycle, a low current passes through diodes 64 and 65 and bypass transistors 67–81 as described below; no current then passes through reverse biased diodes 63 and 66.

The maximum output voltage provided between terminals 61 and 62 is determined by the setting of potentiometer 77. When the voltage between output terminals 61a and 62a rises above 400 Vpp (depending upon the potentiometer setting), the voltage supplied to the base of power transistor 67 becomes sufficiently high to turn on transistor 67. When transistor 67 turns on, Zener diode 80 breaks down and supplies a current to the bases of bypass transistors 68 to 71, turning them on. Resistors 72–76 are selected to ensure that bypass transistors 68–71 turn on whenever transistor 67 is on and to limit the current flow to within the power handling capabilities of the bypass transistors. Resistors 73–76 are selected to pass current equally through the bypass transistors.

When on, bypass transistors 68–71 provide a lower impedance path from node 83 to node 84 than across output terminals 61a and 62a. Thus, bypass transistors 68–71 (and resistors 73–76) when on, act to shunt current from the output terminals and prevent the voltage between terminals 61a and 62a from rising. If this voltage begins to rise, transistor 67 conducts additional current into the bases of bypass transistors 68–71, further turning on those transistors, thereby reducing their impedance and causing those transistors to pass more current. The greater current flow limits the voltage rise between terminals 61a and 62a.

The voltage at output terminal 61a remains constant until later in the AC cycle, when the voltage at node 61, and therefore output terminal 83, falls. The current through the voltage divider drops and the voltage supplied to the base of transistor 67 then falls, turning off transistor 67. Zener diode 80 then ceases to conduct current, turning off bypass transistors 68–71.

It will of course be recognized that the output voltage is limited only during those cycles when the generator and instrument are open-circuited. As shown in FIG. 4, once the instrument is brought into contact with a patient's tissue, the load resistance decreases to the range of 300–400 ohms or less. The voltage output by the generator thus drops to its "fully loaded" range, typically near or under 400 Vpeak-to-peak.

Figure 6:
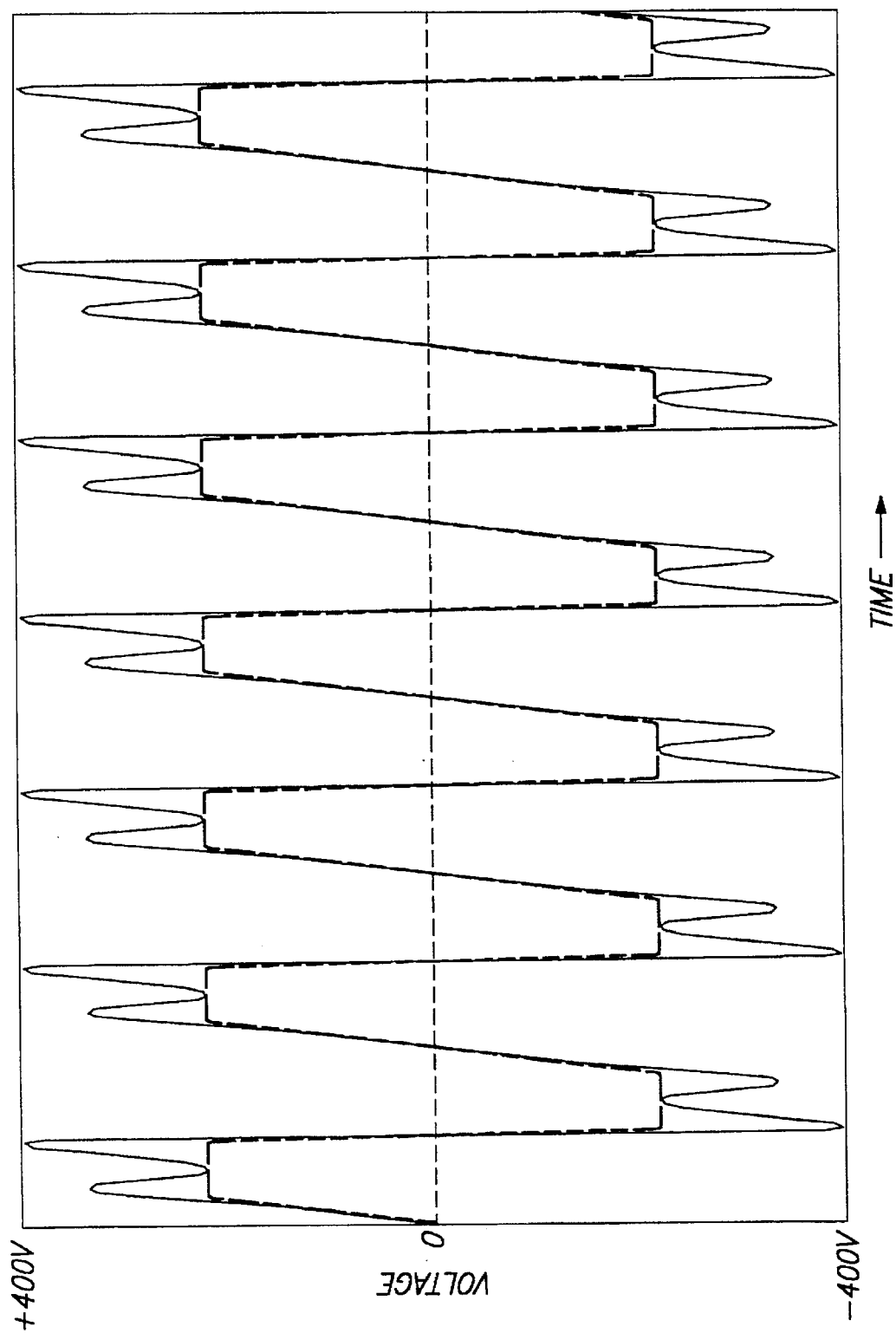
FIG. 6 shows a comparison of the input and output voltage waveforms, under open-circuit conditions, obtained from the adaptor constructed in accordance with FIG. 5.

Due to the symmetry of circuit 60, when the voltage at node 62 rises to the 400 Vpp, the voltage output at output terminal 62a is similarly clipped. FIG. 6 provides a comparison of the input voltage waveform form from the conventional electrosurgical generator (shown in solid line) to the output voltage waveform supplied by adaptor 30 to an electrosurgical instrument (shown in dotted line) for open-circuit conditions as observed on an oscilloscope.

In a preferred embodiment of circuit 60, diodes 63–66 are rated at 200 Vpeak, 6 A and may be commonly packaged as a bridge rectifier. Transistors 67–71 have a 0.08 A capacity at 200 Vpeak, such as part number BUZ406, available from Motorola, Inc., Schaumburg, Ill. Resistor 72 has a resistance of 13 kΩ, while resistors 73–76 have resistances of 10 kΩ. Resistor 78 has a resistance of 47 kΩ, while resistor 79 has a resistance of 13 kΩ. Capacitors 81 and 82 have capacitances of 1 μf at 200 V and 1200 pf, respectively. Zener diode has a breakdown voltage of 12 V. Potentiometer 77 comprises a 100 kΩ adjustable resistance and can be adjusted to vary the maximum output voltage between 70 and 200 Vpeak. If desired, potentiometer 77 may be replaced with a suitable fixed resistance to provide a non-adjustable maximum output voltage. Heat sink 85 comprises a solid block of aluminum having a volume of between 25 cm$^3$ and 50 cm$^3$. Circuit 60 may optionally include a thermal switch to interrupt the circuit if the temperature of the heat sink exceeds, for example, 80° C.

One skilled in the art of circuit design will appreciate that circuit 60 could be readily modified to change the type or number of transistors to accommodate various current capabilities as may be required for a particular standard electrosurgical generator.

One skilled in the art will appreciate that the present invention can be practiced by other than the described embodiments, which are presented for purposes of illustration and not of limitation, and that the present invention is limited only by the claims that follow.

What is claimed is:

1. An adaptor for coupling between an electrosurgical generator and a hemostatic bipolar surgical instrument, the adaptor comprising:

input terminals for coupling the adaptor to the electrosurgical generator;

output terminals for coupling the adaptor to the hemostatic bipolar instrument; and a voltage limiting circuit coupled between the input terminals and the output terminals, the voltage limiting circuit including first and second output nodes, the voltage limiting circuit accepting an input voltage waveform from the electrosurgical generator and supplying an output voltage waveform to the hemostatic bipolar instrument proportional to the input voltage waveform when the input voltage is less than or equal to a predetermined voltage value, the voltage limiting circuit shunting current between the first and second output nodes to supply a clipped output voltage waveform to the hemostatic bipolar instrument when the input voltage waveform exceeds the predetermined voltage value.

2. An adaptor as defined in claim 1 wherein the electrosurgical generator has a monopolar output jack and a return jack and the input terminals of the adaptor are coupled to the monopolar output jack and the return jack, and wherein the predetermined value is selected so that the clipped voltage waveform supplied to the hemostatic bipolar instrument is equal to or less than 120 VRMS with a crest factor near unity.

3. An adaptor as defined in claim 1, wherein the voltage limiting circuit comprises:

a transformer having primary and secondary windings, the input voltage waveform of the electrosurgical generator applied across the primary winding;

a rectifier bridge coupled to the secondary winding, the rectifier bridge including first and second nodes which comprise the first and second output nodes; and means coupled to the first and second nodes for limiting the voltage across the first and second nodes.

4. An adaptor as defined in claim 3 wherein the means for limiting the voltage across the first and second nodes comprises:

a transistor having a base, an emitter and a collector, the collector connected to the first node and the emitter connected to the second node;

a diode having a preselected breakdown voltage, the cathode of the diode connected to the collector and the anode of the diode connected to the base, wherein the breakdown voltage determines RMS voltage and crest factor of the clipped voltage waveform; and a resistor connected to the base of the transistor and the second node.

5. An adaptor as defined in claim 3 wherein the secondary winding further comprises a plurality of user-selectable taps, each of the plurality of taps corresponding to a different ratio of secondary to primary windings.

6. An adaptor as defined in claim 3 wherein the means for limiting the voltage across the first and second nodes comprises a plurality of user-selectable diodes, each of the plurality of diodes having a different breakdown voltage, so that degree of clipping of the input voltage waveform of the electrosurgical generator can be varied.

7. An adaptor as defined in claim 1 wherein the electrosurgical generator has bipolar output jacks and the input terminals of the adaptor are coupled to the bipolar output jacks, and wherein the predetermined value is selected so that the clipped output voltage waveform supplied to the hemostatic bipolar instrument is equal to or less than 400 Vpeak-to-peak.

8. An adaptor as defined in claim 1, wherein the voltage limiting circuit comprises:

a rectifier bridge including first and second nodes which comprise the first and second output nodes; and means coupled to the first and second nodes for limiting the voltage across the first and second nodes.

9. An adaptor as defined in claim 8 wherein the means for limiting the voltage across the first and second nodes comprises:

a switching circuit; and a bypass transistor having a base, an emitter and a collector, the collector of the bypass transistor coupled to first node, the emitter of the bypass transistor coupled to the second node, and the base of the bypass transistor coupled to the switching circuit.

10. An adaptor as defined in claim 9 wherein the switching circuit comprises:

a power transistor having a base, an emitter and a collector, the collector connected to the first node and the emitter connected to the second node;

a voltage divider connected to the base of the power transistor; and a diode having a preselected breakdown voltage, the cathode of the diode connected to the emitter and the anode of the diode coupled to the base of the bypass transistor.

* * * * *